(12) United States Patent
Black et al.

(10) Patent No.: US 11,484,634 B2
(45) Date of Patent: Nov. 1, 2022

(54) CHEST TUBE AIR LEAK DETECTION SYSTEM

(71) Applicants: C. Thomas Black, Arlington, TX (US); Stephen David Black, Arlington, TX (US)

(72) Inventors: C. Thomas Black, Arlington, TX (US); Stephen David Black, Arlington, TX (US)

(*) Notice: Subject to any disclaimer, the term of this patent is extended or adjusted under 35 U.S.C. 154(b) by 250 days.

(21) Appl. No.: 16/886,476

(22) Filed: May 28, 2020

(65) Prior Publication Data

US 2021/0369925 A1    Dec. 2, 2021

(51) Int. Cl.
*A61M 1/04*     (2006.01)
*A61M 39/22*    (2006.01)
*A61M 1/00*     (2006.01)
*A61M 39/10*    (2006.01)

(52) U.S. Cl.
CPC ............ *A61M 1/04* (2013.01); *A61M 1/0001* (2013.01); *A61M 39/10* (2013.01); *A61M 39/223* (2013.01); *A61M 2205/15* (2013.01); *A61M 2205/6063* (2013.01)

(58) Field of Classification Search
CPC ...... A61M 1/04; A61M 39/10; A61M 39/223; A61M 2205/15; A61M 2205/6063; A61M 1/734; A61M 2205/3334; A61M 1/61; A61M 1/60; A61M 1/64

See application file for complete search history.

(56) References Cited

U.S. PATENT DOCUMENTS

| | | | | |
|---|---|---|---|---|
| 3,750,692 A | * | 8/1973 | Tibbs ..................... | A61M 1/61 141/59 |
| 4,195,633 A | * | 4/1980 | Nehring .................. | A61M 1/61 604/320 |
| 4,439,190 A | * | 3/1984 | Protzmann ............... | A61M 1/61 248/339 |
| 4,747,844 A | * | 5/1988 | Elliott .................... | A61M 1/61 604/319 |

(Continued)

FOREIGN PATENT DOCUMENTS

| | | | | |
|---|---|---|---|---|
| GB | 2171311 A | * | 8/1986 | .......... A61M 1/0013 |
| WO | WO-0183003 A1 | * | 11/2001 | .......... A61M 1/0017 |

(Continued)

*Primary Examiner* — Susan S Su
*Assistant Examiner* — Eric Rassavong
(74) *Attorney, Agent, or Firm* — Law Office of Jeff Williams PLLC; J. Oliver Williams

(57) ABSTRACT

A gas collection unit for use in monitoring and tracking a discharge of air from a patient includes a housing, a set of valves, and a plurality of tubes. The housing contains a first chamber, a second chamber, and a third chamber wherein the chambers are in fluid communication with one another. The housing includes a fluid in the first chamber and the second chamber. The first valve regulates the passage of air flow from the patient into the first chamber and is located within a first tube coupled to the housing. The second valve is in communication with the second chamber. The second valve being configured to regulate the passage of air exiting the first chamber. The second chamber is subjected to a suction. The gas collection unit is operable with an air collection device as a retrofitted item.

19 Claims, 17 Drawing Sheets

(56) References Cited

U.S. PATENT DOCUMENTS

| | | | | |
|---|---|---|---|---|
| 4,781,707 A * | 11/1988 | Boehringer | ............. | A61M 1/61 604/319 |
| 4,822,346 A * | 4/1989 | Elliott | ................ | A61M 1/61 604/319 |
| 4,898,593 A * | 2/1990 | Swisher | ................ | A61M 1/61 D24/169 |
| 5,114,416 A * | 5/1992 | Karwoski | ............... | A61M 1/61 604/320 |
| 5,300,050 A * | 4/1994 | Everett, Jr. | ............ | A61M 1/61 604/320 |
| 5,865,408 A * | 2/1999 | Swisher | ................ | F16M 11/22 248/188.1 |
| 6,902,550 B2 * | 6/2005 | Want | ................ | A61M 1/61 604/321 |
| 6,976,977 B2 * | 12/2005 | Yam | .................. | A61M 1/732 604/320 |
| 7,028,707 B2 * | 4/2006 | Corbeil | ................ | A61M 1/61 137/493 |
| 9,888,870 B2 * | 2/2018 | Miserlis | ................ | A61B 5/08 |
| 10,143,781 B1 * | 12/2018 | Pollen | ................ | A61M 1/61 |
| 10,195,404 B2 * | 2/2019 | Grziwa | ................ | A61M 1/73 |
| 2002/0072722 A1 * | 6/2002 | Swisher | ................ | A61M 1/61 604/319 |
| 2002/0173757 A1 * | 11/2002 | Swisher | ................ | A61M 1/61 604/326 |
| 2003/0212337 A1 * | 11/2003 | Sirokman | ............... | A61M 1/61 600/529 |
| 2004/0260255 A1 * | 12/2004 | Charlez | ................ | A61M 1/743 604/317 |
| 2008/0082061 A1 * | 4/2008 | Zhou | .................. | A61M 27/00 604/319 |
| 2010/0130948 A1 * | 5/2010 | Daly | .................. | A61M 1/61 604/319 |
| 2013/0110057 A1 * | 5/2013 | Croteau | ................ | A61L 29/08 604/327 |
| 2015/0174305 A1 * | 6/2015 | Bharat | ................ | A61M 1/73 604/26 |
| 2017/0348475 A1 * | 12/2017 | Hiemenz | ............... | A61M 3/022 |
| 2018/0050135 A1 * | 2/2018 | Reinboth | ............... | A61M 1/631 |

FOREIGN PATENT DOCUMENTS

| | | | | |
|---|---|---|---|---|
| WO | WO-03103747 A1 * | 12/2003 | .......... | A61M 1/0013 |
| WO | WO-2009005424 A1 * | 1/2009 | .......... | A61M 1/0013 |
| WO | WO-2017155994 A1 * | 9/2017 | .......... | A61M 1/0001 |
| WO | WO-2018022489 A1 * | 2/2018 | .......... | A61M 1/0013 |

* cited by examiner

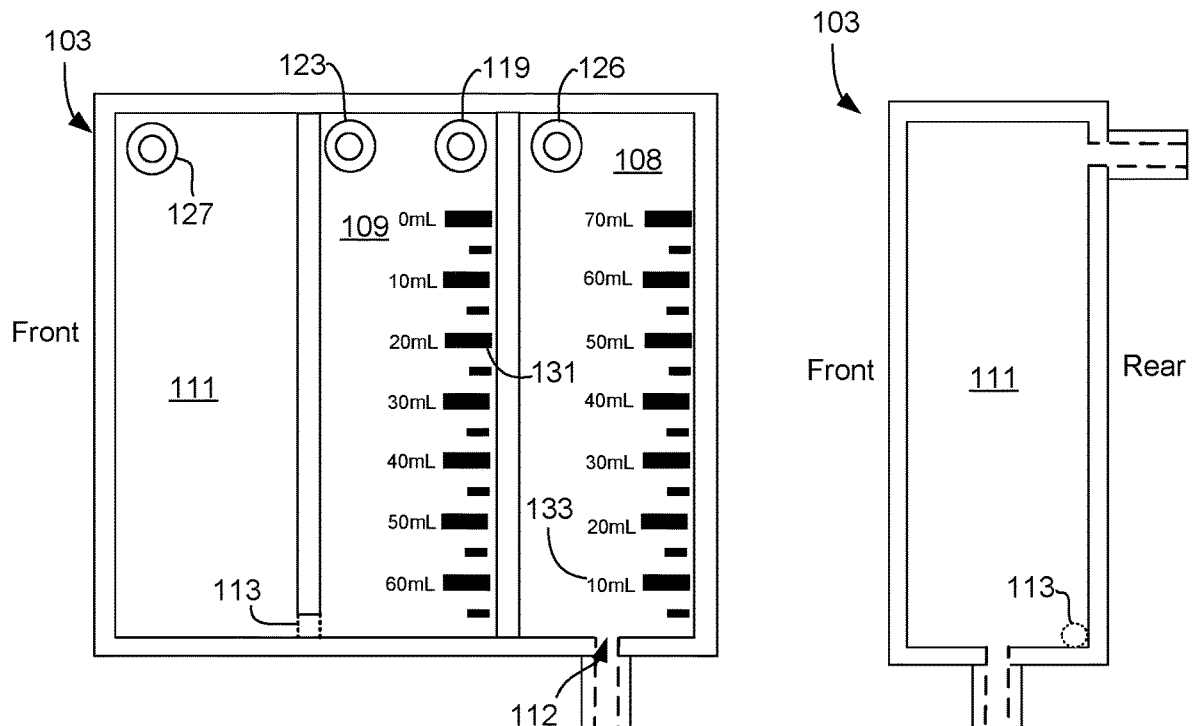
FIG. 6
FIG. 7
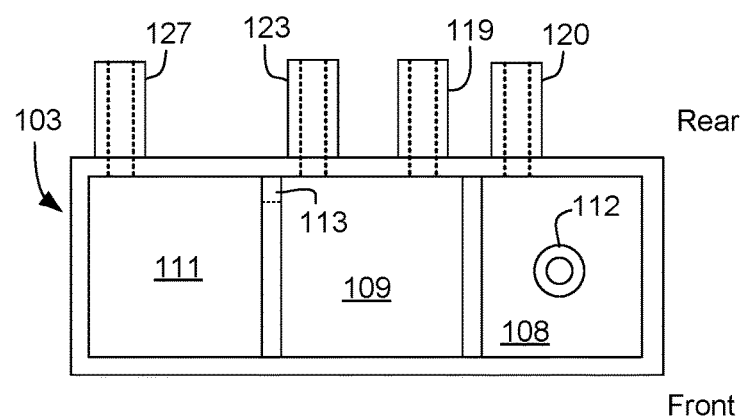
FIG. 8

CHEST TUBE AIR LEAK DETECTION SYSTEM

BACKGROUND

1. Field of the Invention

The present application relates to a device that quantitatively measures gas output. It may be utilized in situations including postoperative thoracic surgery and more particularly for the quantitation of air leakage from the lungs following surgery or injury.

2. Description of Related Art

'Cardiothoracic surgery' is a field of medicine that involves the surgical treatment of specific organs within the thorax, i.e., the heart and associated vascular structures. The term 'thoracic surgery' relates more particularly to procedures involving the parenchyma of the lungs, the esophagus, the thymus, etc. The thoracic cavity is a potential space surrounded by the pleura, a thin layer of membranous tissue. The visceral pleura comprises the surface of the lung while the parietal pleura covers the undersurface of the ribs, the intercostal muscles, the diaphragm, etc. Thoracic surgical procedures nearly always violate the parietal and often the visceral pleura allowing air to enter the thoracic cavity. Similarly, when penetrating thoracic injuries violate the parietal and visceral pleurae, leakage of external and inhaled air, respectively, into the thoracic cavity is the result. Regardless of the mechanism, gas accumulating in the thoracic cavity results in collapse of the lung, so accumulating air should be evacuated promptly to prevent respiratory compromise. Following either thoracic surgery or pulmonary injury, a flexible plastic tube is generally inserted between the ribs into the thoracic cavity. The tube is then attached to one of several devices and suction applied, to evacuate any gas within the thoracic cavity. Once the gas is completely evacuated, the damage causing the air leak has healed, and the leakage of air has ceased, the tube is no longer needed and may be removed.

Referring now also to FIG. 1 in the drawings, a schematic of an air evacuation device 99 used to collect fluid and to monitor gas leakage is illustrated. In the basic concept, a plurality of containers is aligned in series, each serving a purpose. Generally in operation, a collection tube 96 runs from the patient and enters a collection bottle 97. Evacuated fluid collects by gravity at the bottom of bottle 97, while air passes into tube 94 and thence into bottle 95. The end of tube 94 is submerged beneath a quantity of liquid, which allows the gas passing from bottle 97 to be observed bubbling through the liquid. The liquid in chamber 95 also prevents air from returning through tube 94 into bottle 97 and thence into the thoracic cavity of the patient. Expelled gas passes from chamber 95 into jar 93 through tube 87. Stronger suction than what is needed in the system is supplied through tube 89. Since chamber 93 is also exposed to the atmosphere through tube 91, adjusting the depth of tube 91 below the surface of the water will regulate the actual negative pressure present in chamber 93—the deeper the tube, the more negative the air pressure will be in chamber 93 and therefor in chambers 95 and 97. As noted, FIG. 1 shows schematically the current method of removing and qualitatively monitoring leaked air. This device in its several current forms provides a crude assessment of the readiness of the patient to have his or her chest tube removed.

Referring now also to FIGS. 2-4 in the drawings, an exemplary embodiment of a gas collection device of FIG. 1 is illustrated. The basic function of embodiment 99 is shown in FIG. 2 with representative containers depicted to more easily compare with the device of FIG. 1. Current devices facilitating the design shown in FIGS. 1 and 2 employ the production and use of a disposable plastic device as depicted in embodiment 88 and 87 of FIGS. 3 and 4, respectively.

Determination of air leakage from the patient involves checking periodically the water-filled portion of chamber 95 in FIG. 3 to see whether gas bubbles are exiting. This method is notoriously inaccurate for this purpose. The leak may be so slow or intermittent or so positional that no bubbles may be seen escaping during the brief period of scrutiny. If bubbles are not seen, but the observer is still suspicious that air is leaking, the tube may be taken off of suction temporarily—some caregivers advocate clamping or otherwise occluding tube 96, a potentially dangerous maneuver—and obtaining a chest radiograph several hours later. Others will wait an additional 24-48 hours after the last bubbling is seen simply as a precaution. These methods are highly subjective and involve extra expense, additional hospitalization, increased risk, and prolonged patient discomfort.

In an effort to make the decision regarding chest tube removal more objective, electronic devices have been created that follow the same basic principles of device 99. Such devices have one or more sensors to continuously measure gas leakage, and various types of digital displays and reports may be generated to assess the amount of escaped gas. Although there are some advantages to such electronic devices, it is understood that these are still the same general set up as device 99. Further disadvantages of such electronic devices include the expense, the need for additional training, and the unnecessary tendency to overcomplicate matters. Furthermore, such devices are obviously dependent upon electricity and require either batteries and/or current from the power grid. Electronic sensors can stop working, and their use around aqueous liquids can be hazardous. The increased expense and therefore limited availability of such devices is obvious.

Although strides have been made to provide improved data related to the measurement of air leakage from a patient, shortcomings remain. It is desirable that an assembly be provided that is safe, inexpensive, and independent of electricity, yet capable of measuring air leakage accurately over time.

SUMMARY OF THE INVENTION

It is an object of the present application to provide a gas collection unit. This unit is configured to capture and display, in visual form, the volume of gas evacuated from the thoracic cavity. The unit is configured to track volumetric changes over time and can be reset to track a new set of volumetric changes over a subsequent time period. The gas collection unit may be utilized in conjunction with compatible air evacuation devices. Because of contact with bodily fluids and gases, however, the unit is not intended for reuse with other patients. The unit is configured to use conventional principles of fluid mechanics to monitor volumetric changes without the need of electricity.

It is a further object of the present application to combine the gas collection unit with an existing air evacuation device to form a chest tube air leak detection system. Such a system is a combination of an air evacuation device and the gas collection unit of the present application. The gas collection unit is integrated into the construction of the air evacuation device and is operable within a plurality of modes of use. Operation of selected valves switches the modes of use.

Ultimately the invention may take many embodiments. In these ways, the present invention overcomes the disadvantages inherent in the prior art. The more important features have thus been outlined in order that the more detailed description that follows may be better understood and to ensure that the present contribution to the art is appreciated. Additional features will be described hereinafter and will form the subject matter of the claims that follow.

Many objects of the present application will appear from the following description and appended claims, reference being made to the accompanying drawings forming a part of this specification wherein like reference characters designate corresponding parts in the several views.

Before explaining at least one embodiment of the present invention in detail, it is to be understood that the embodiments are not limited in their application to the details of construction and the arrangements of the components set forth in the following description are illustrated in the drawings. The embodiments are capable of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the various purposes of the present design. It is important, therefore, that the claims be regarded as including such equivalent constructions insofar as they do not depart from the spirit and scope of the present application.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

FIG. 6 is a front view of a housing in the gas collection unit of FIG. 5.

FIG. 7 is a side view of the housing in FIG. 6.

FIG. 8 is a top view of the housing of FIG. 6.

Figure 1:
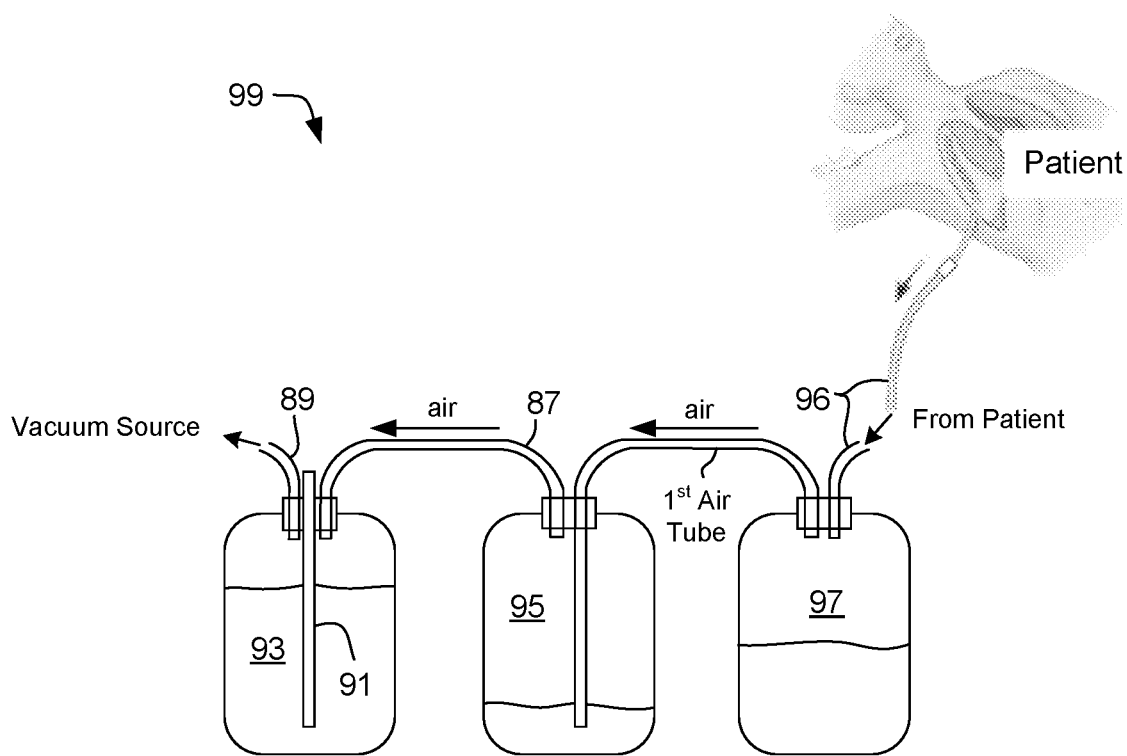
FIG. 1 is a schematic of an air evacuation device for use whenever gas must be evacuated from the thoracic cavity.
Figure 2:
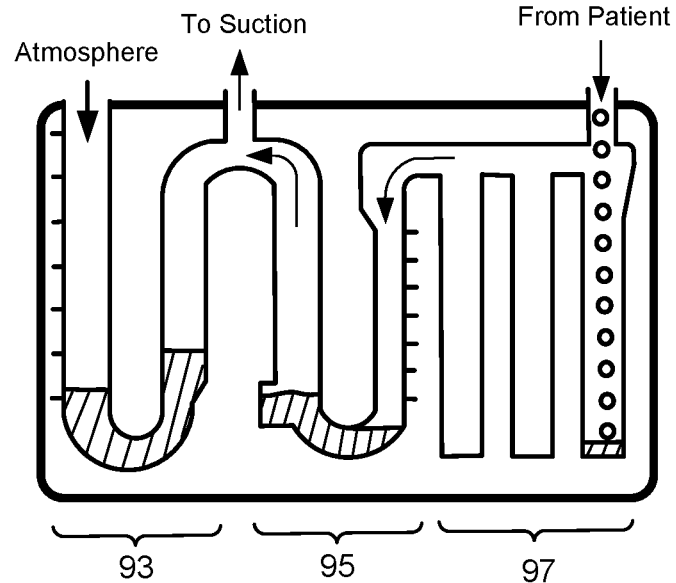
FIG. 2 is an exemplary schematic of the air collection device of FIG. 1.
Figure 3:
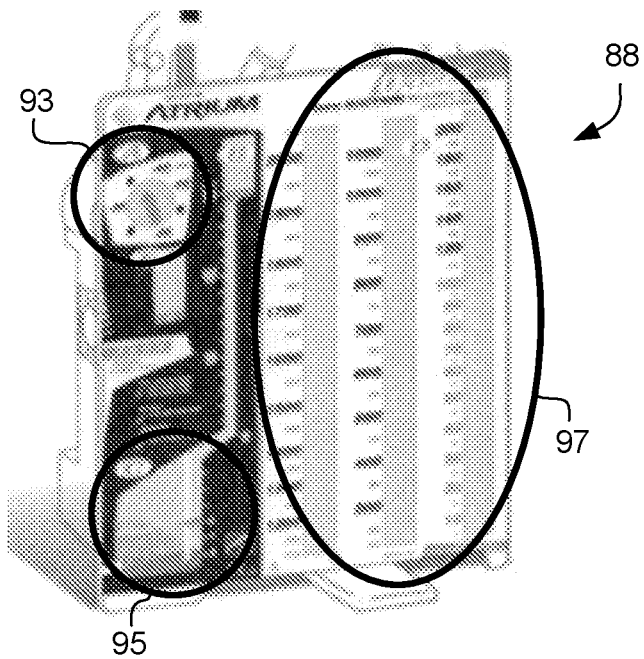
FIGS. 3 and 4 are perspective views of an embodiment of the exemplary schematic of FIG. 2.
Figure 4:
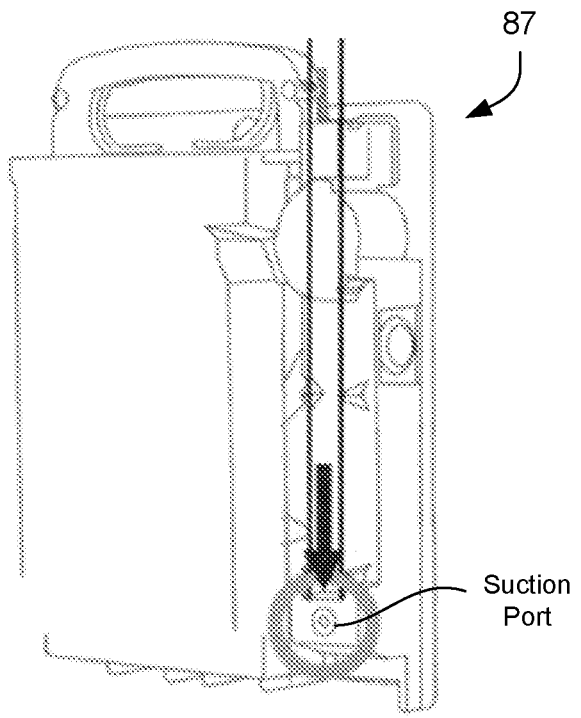

While the embodiments and method of the present application are susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the embodiments described herein may be oriented in any desired direction.

The embodiments and method in accordance with the present application overcome one or more of the above-discussed problems commonly associated with air evacuation devices discussed previously. In particular, the gas collection unit of the present application is configured to capture and display, in visual form, the volume of air leaked from the lungs. The unit is configured to track volumetric changes over time and can be reset to track further volumetric changes over a subsequent time period. The gas collection unit is configured to operate in conjunction with an air evacuation device. These and other unique features are discussed below and illustrated in the accompanying drawings.

The embodiments and method will be understood, both as to its structure and operation, from the accompanying drawings, taken in conjunction with the accompanying description. Several embodiments of the assembly may be presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

The embodiments and method of the present application are illustrated in the associated drawings. The gas collection unit includes a housing containing a first, a second, and a third chamber. The second and third chambers are in fluid communication with one another via a passage along the bottom interior surface. The housing includes a fluid within the second chamber that selectively transitions to the third chamber over time with the collection of air in the second chamber. The unit also includes a 'collection valve' to redirect the passage of airflow from the patient into the first chamber. A 'test valve' is configured to control the passage of air exiting the first chamber. A 'reset valve' is in communication with the second chamber and is configured to allow restoration of the system to its initial status. The third chamber is subjected to regulated suction. Additional features and functions are illustrated and discussed below.

Referring now to the Figures wherein like reference characters identify corresponding or similar elements in form and function throughout the several views. The following Figures describe embodiments of the present application and its associated features. With reference now to the FIGS. 5 through 20, embodiments of the present application are herein described. It should be noted that the articles "a", "an", and "the", as used in this specification, include plural referents unless the content clearly dictates otherwise.

Figure 5:
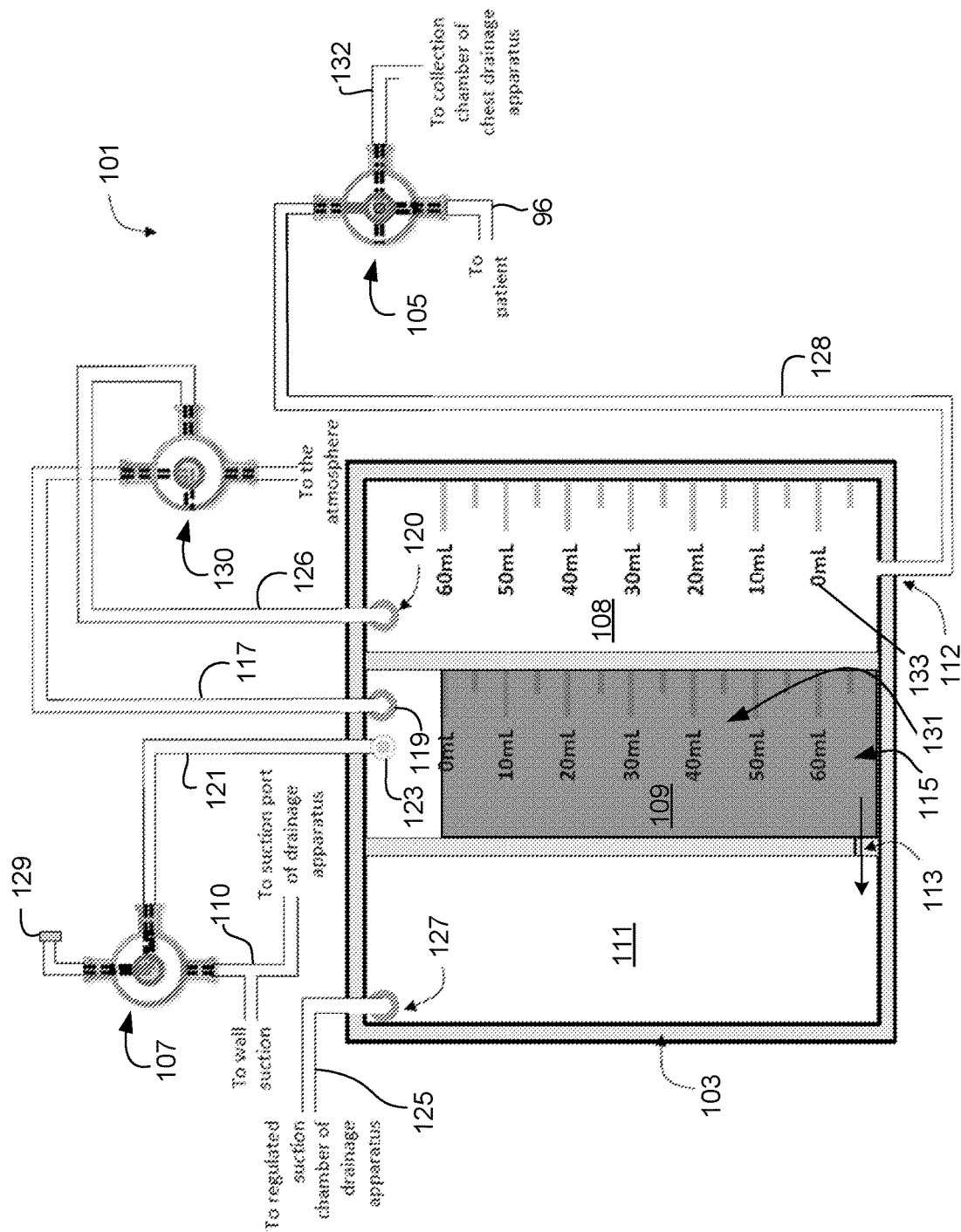
FIG. 5 is a front view of a gas collection unit according to an embodiment of the present application.

Referring now to FIG. 5 in the drawings, an air collection unit 101 is illustrated. Unit 101 includes a housing 103 and tubing 128 that leads to a collection valve 105, tubing 126 and 117 that lead to a test valve 130, and tubing 121, that leads to a reset valve 107. Unit 101 is configured to receive discharged air from the patient through valve 105 and to measure the accumulation of a volume of air over a period of time. Discharge of air from the patient may be slow and almost unnoticeable unless the medical professional happens to be there to observe it or is monitoring the circuit continuously. Routing the air through unit 101 provides a function of measuring that does not rely on visual observation of bubbles but rather allows the medical professional to note a start level and an end level over a period of time. Unit 101 is operable without electrical power.

The relationships of the three valves 105, 130, and 107 to housing 103 are also illustrated in FIG. 5. These valves control the flow of air and fluid through the apparatus. Valve 105 is of a three-port three-way configuration while valves 130 and 107 are of a three-port two-way configuration.

Referring to FIGS. 6-8 in the drawings, housing 103 is illustrated in detail. This housing includes a first chamber 108, a second chamber 109, and a third chamber 111. Chambers 109 and 111 are in fluid communication with one another through passage 113. Passage 113 is located along a lower interior surface of housing 103. A fluid 115 is located within second chamber 109 and is permitted to pass freely from chamber 109 into chamber 111 with the introduction of air into chamber 108 when valve 130 is positioned appropriately.

It is noted that housing 103 also includes measuring indicia 131/133 to permit a medical professional to view and measure the fluid levels within chambers 109/108. In operation, as air is collected in chamber 109, fluid 115 transitions to chamber 111 and the fluid level within chamber 109 decreases. The amount of air filling second chamber 109 is measured via indicia 131. It is understood that indicia 131 for quantifying air leakage may be located on chamber 109 and/or chamber 111.

Housing 103 also includes a plurality of ports for the coupling of one or more tubes. Air discharged from the patient is selectively routed to and from housing 103 via a plurality of tubes releasably coupled to the ports. Ports 112 and 120 exit from chamber 108. Tubing 128 couples valve 105 to port 112 while tubing 126 couples valve 130 to port 120. Ports 119 and 123 exit from chamber 109. Tubing 117 couples valve 130 to port 119 while tubing 121 couples valve 107 to port 123. Lastly, port 127 exits from chamber 111 and is coupled to tubing 125. Ports 120, 119, 123, and 127 are ideally located in the upper portion of their respective chambers and are not in continuity with fluid 115. This allows air only to pass therethrough as opposed to port 112, which, being dependent, allows fluid to pass therethrough.

Figure 9A:
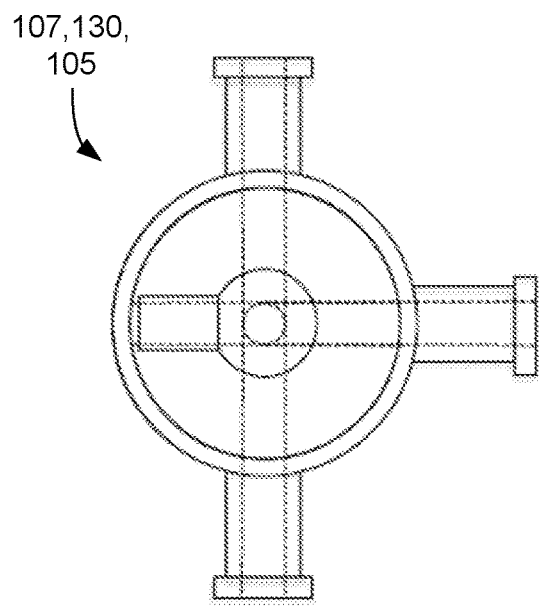
FIGS. 9A-9C are depictions of the construction of the valves required to operate the device in its various functional modes.
Figure 9B:
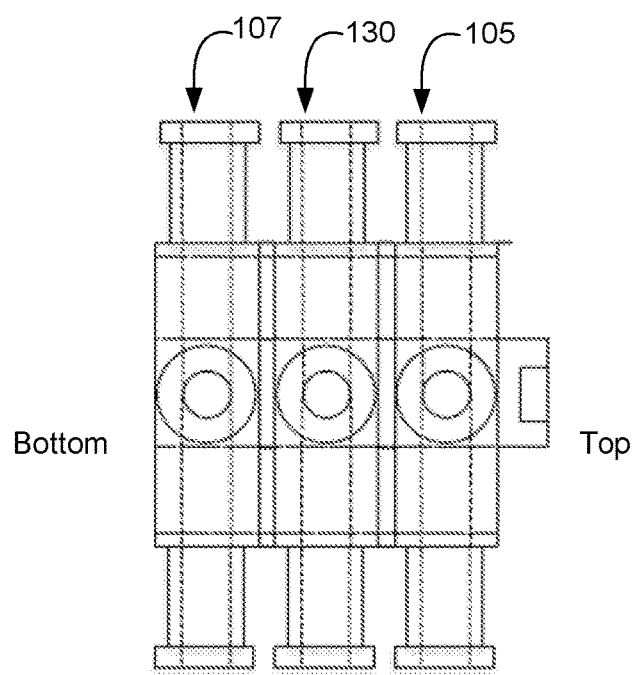
Figure 9C:
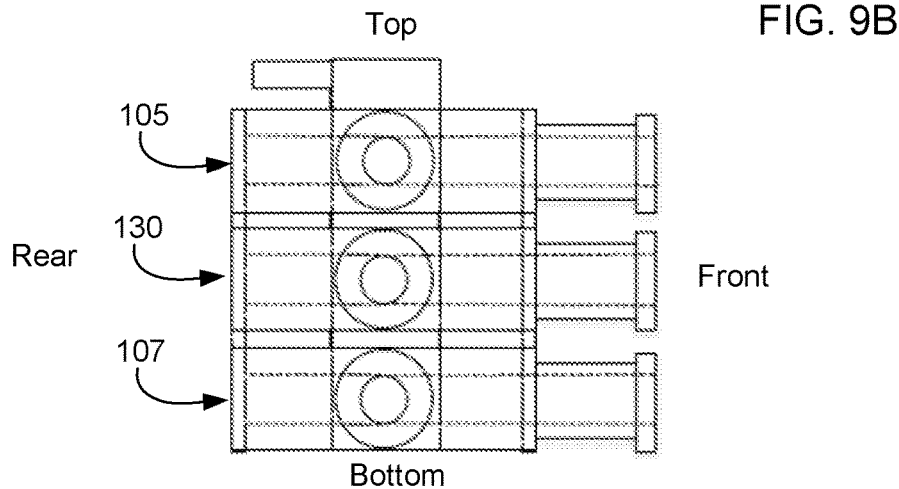

Similarly, FIGS. 9A-9C depict schematically the valves shown in FIG. 5. It is understood that these three valves, 105, 130, and 107, may be coupled together on the same central axis such that rotating the knob 90 degrees in a clockwise direction advances the valves simultaneously to the next position of each initiating the next mode of use. Individually operable valves independent of one another are also permitted.

Figure 10:
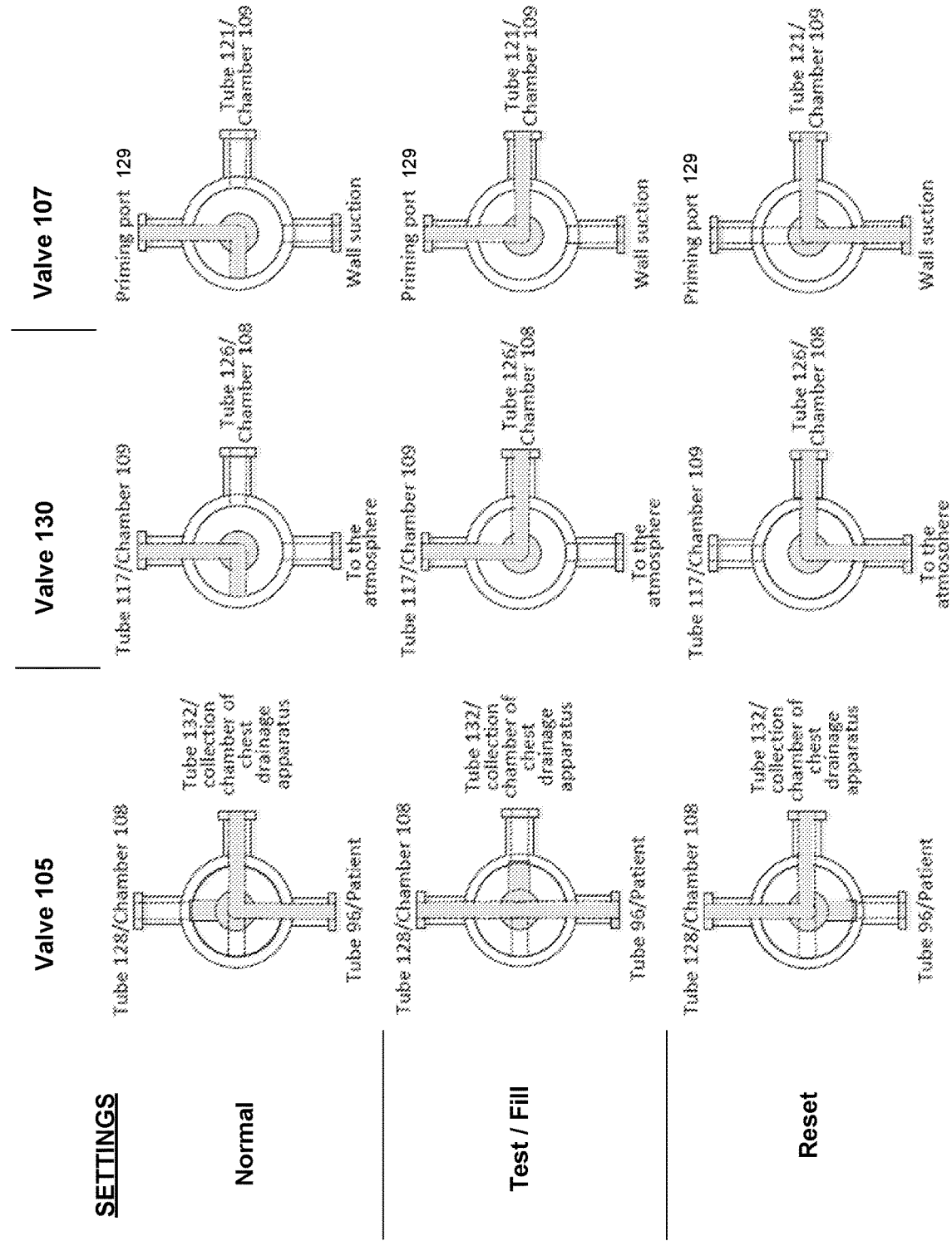
FIG. 10 is a depiction of the settings of the valves shown in FIGS. 9A-9C for use during different modes of use.

It is understood that these three valves operate in concert in three distinct modes, Normal/Fill, Test, and Reset. The configuration of the valves at each mode is depicted in FIG. 10.

Regarding valve 105: in Normal/Fill mode, valve 105 directs air and fluid from the patient's chest into the drainage collection apparatus through tubing 132. Also in this mode, chamber 109 may be filled through priming port 129. In Test mode, valve 105 diverts air or fluid from the chest drainage collection apparatus into the leak detection apparatus through tubing 128. Reset mode is employed only momentarily, just long enough to allow any fluid that has collected in chamber 108 during the test to drain through valve 105 into the collection chamber of the chest drainage collection apparatus through tubes 128 and 132 and for fluid 115 displaced into chamber 111 to return to chamber 109 through passage 113.

Regarding valve 130: in Normal/Fill mode, valve 130 is closed. In Test mode, valve 130 allows free communication of air between chambers 108 and 109 through tubes 126 and 117. In Reset mode, valve 130 briefly connects chamber 108 to the atmosphere through tube 126 to allow free drainage of the aforementioned fluid.

Regarding valve 107: in Normal/Fill mode, this valve is closed. Prior to initiating suction, fluid 115 may be placed into chamber 109 through priming port 129 and housing port 123. In Test mode, valve 107 remains closed. In Reset mode, valve 107 briefly connects chamber 109 to wall suction through tubes 121 and 110, causing fluid from chamber 111 to return through passage 113 into chamber 109.

Figure 11:
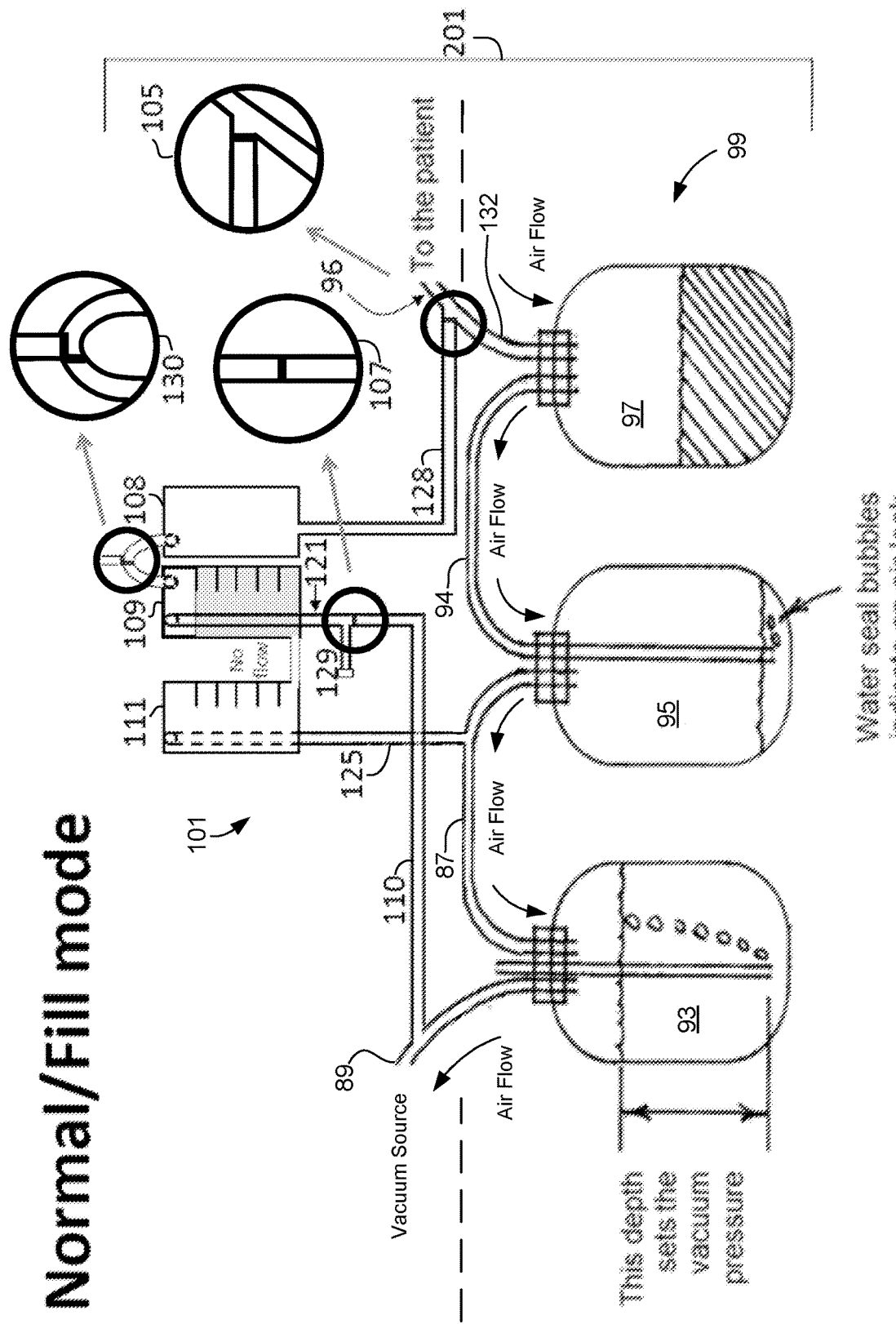
FIG. 11 is a schematic of the gas collection unit of FIG. 5 used in combination with the air evacuation device of FIG. 1 in a first mode of use.
Figure 12:
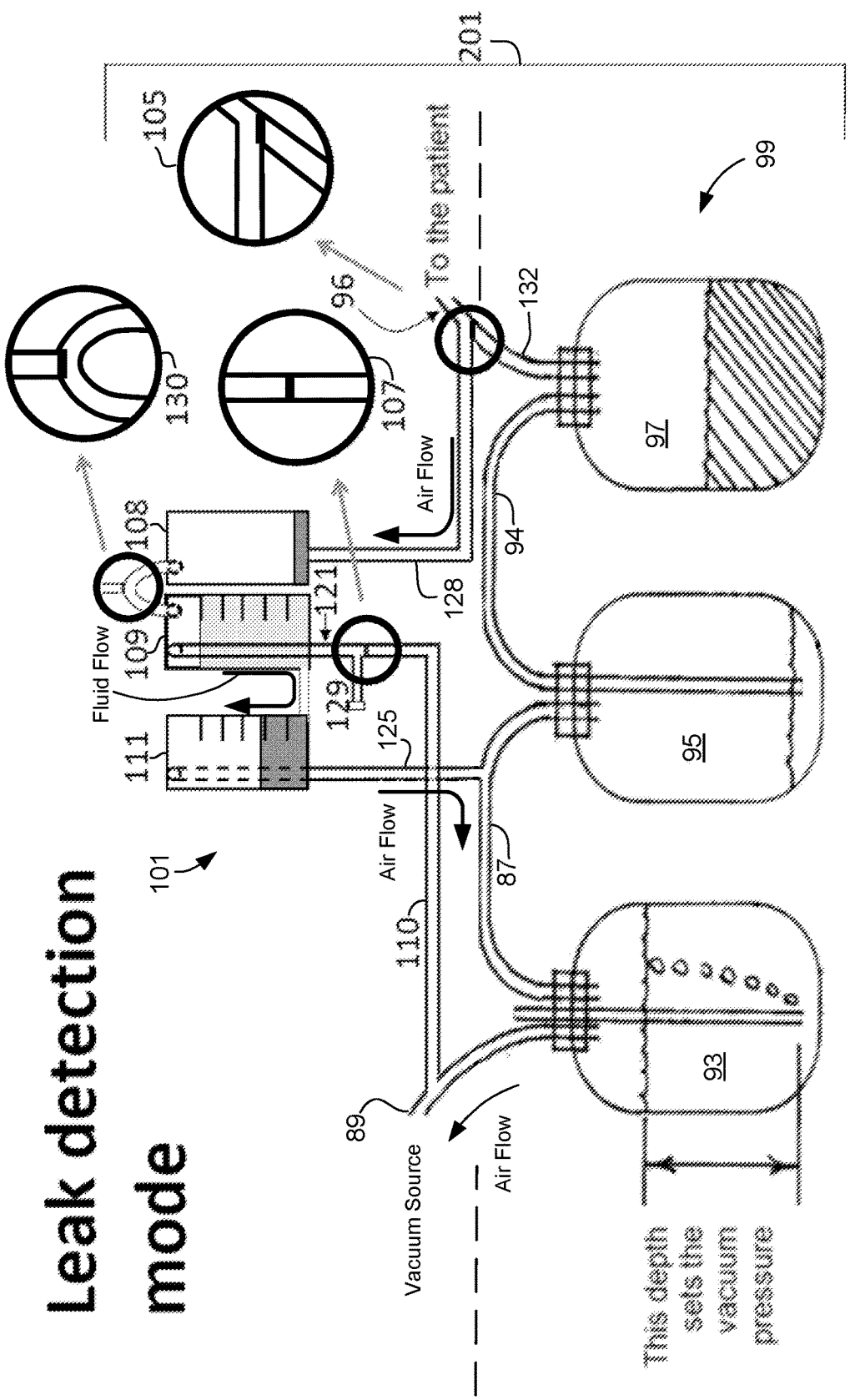
FIG. 12 is a schematic of the gas collection unit of FIG. 5 used in combination with the air evacuation device of FIG. 1 in a second mode of use.
Figure 13:
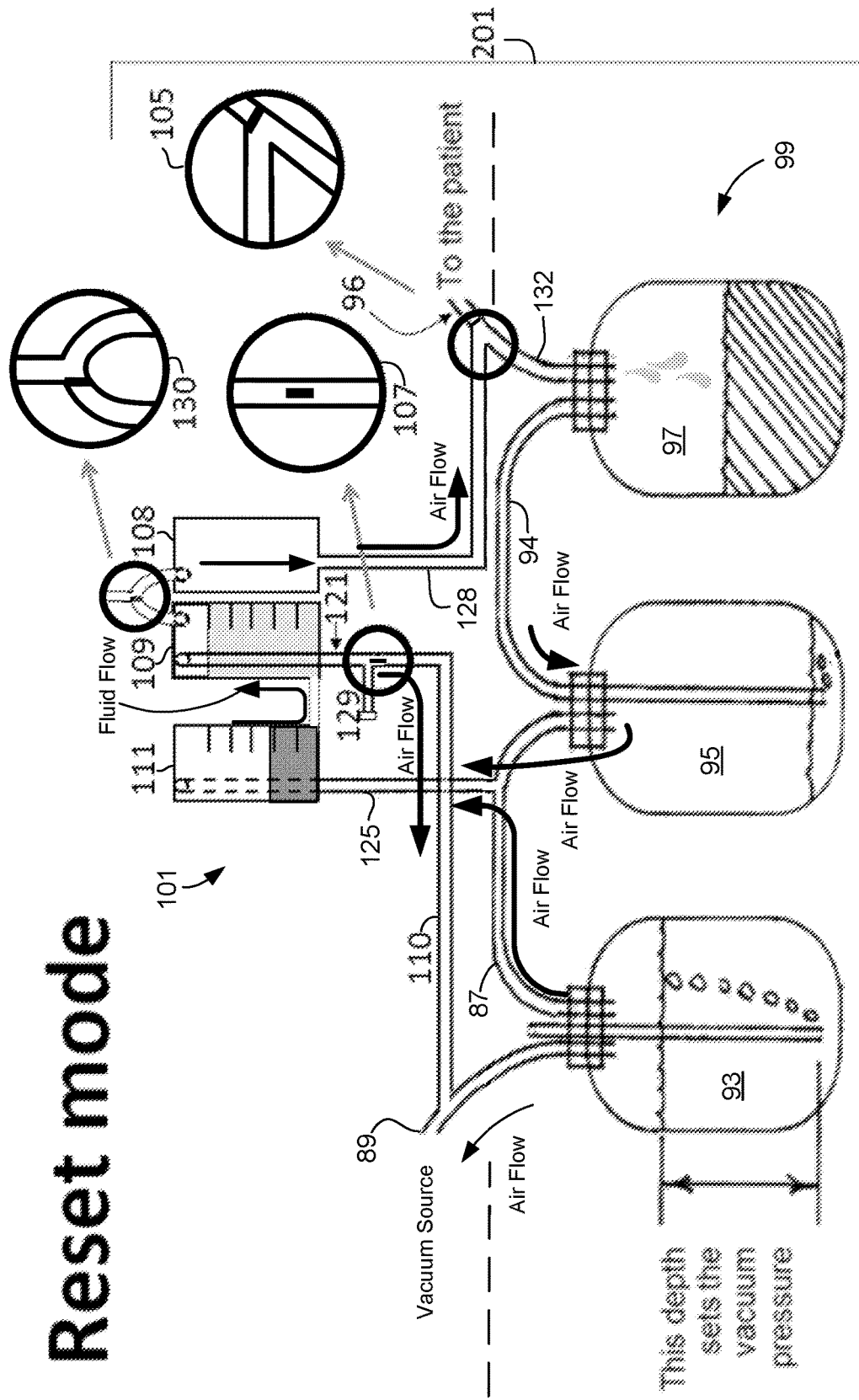
FIG. 13 is a schematic of the gas collection unit of FIG. 5 used in combination with the air evacuation device of FIG. 1 in a third mode of use.

FIGS. 11-13 describe schematically how the chest drainage collection apparatus 99 (below the dashed line) integrates with the leak detection device 101 (above the dashed line) to form unit 201. FIG. 11 depicts the valve settings and airflow in the Normal/Fill mode. In this mode, fluid may be introduced into chamber 109 through priming port 129. Once the vacuum source is activated, air from the patient will pass through collection tube 96 and arrive at valve 105, the junction of tubes 128, 132, and 96. With valve 105 in the proper position, air and fluid are routed into bottle 97. The air passes through the system until it exits through tube 89. In this manner of normal use, valves 105, 130, and 107 are all closed, preventing air from entering chambers 108, 109, and 111. Unit 101 is nonfunctioning in this mode of use, which is appropriate immediately following surgery when discharge of air from the patient is usually greatest. Bubbles are easily visible in chamber 95. As tissue healing progresses over time, the frequency and volume of bubbles decrease and the question of when to remove the chest tube eventually arises. At that time, when bubbles have apparently ceased, the Test mode is initiated, and a quantitative measurement of air leakage is substituted for qualitative observation. Bubbling is normally seen in the water seal chamber. If not, it is time to test for a slow leak. Also, in Normal mode, the attached device is non-functional.

In the Test or Leak Detection Mode shown in FIG. 12, unit 99 monitors and measures a slow discharge of air from the patient. To perform an evaluation, valve 105 is opened so as to prevent air and fluid from traversing further down collection tube 96 into tube 132 and routing the air and possibly fluid into chamber 108. Over time and under regulated suction, any leaked air slowly flows from the patient first into chamber 108, then into chamber 109 thereby displacing fluid into chamber 111 through passage 113. Reset valve 107 remains closed. The medical professional notes the time and ensures that the fluid level reading was zeroed out. Displaced air from chamber 111 passes through tube 125 and into jar 93 before being discharged through vacuum tube 89. After adequate time has elapsed for a reliable test, the medical professional notes the time and volume of air in chamber 109 by referring to indicia 131. From these data, the medical professional can calculate a rate of leakage from the patient and make an objective decision regarding the propriety of chest tube removal.

In the Reset mode shown in FIG. 13, the fluid in chamber 111 can be returned to chamber 109. This can allow for another test to be run or for normal operation to recommence. In Reset mode, valve 107 is momentarily opened and valve 105 closed to the patient. Air then passes from jar 93 through tubes 87 and 125 and into chamber 111. The fluid in chamber 111 transitions back into chamber 109 through passage 113. While resetting chamber 109, bubbles seen in jar 93 indicate a lower regulated degree of suction relative to that present in tube 121 and chamber 109. Bubbles also indicate airflow from the atmosphere into chamber 111, which allows the fluid within to return to chamber 109. Following an unsuccessful test, the system is reset by opening the 'Reset' valve until the fluid has completely returned to the chamber.

Figure 14:
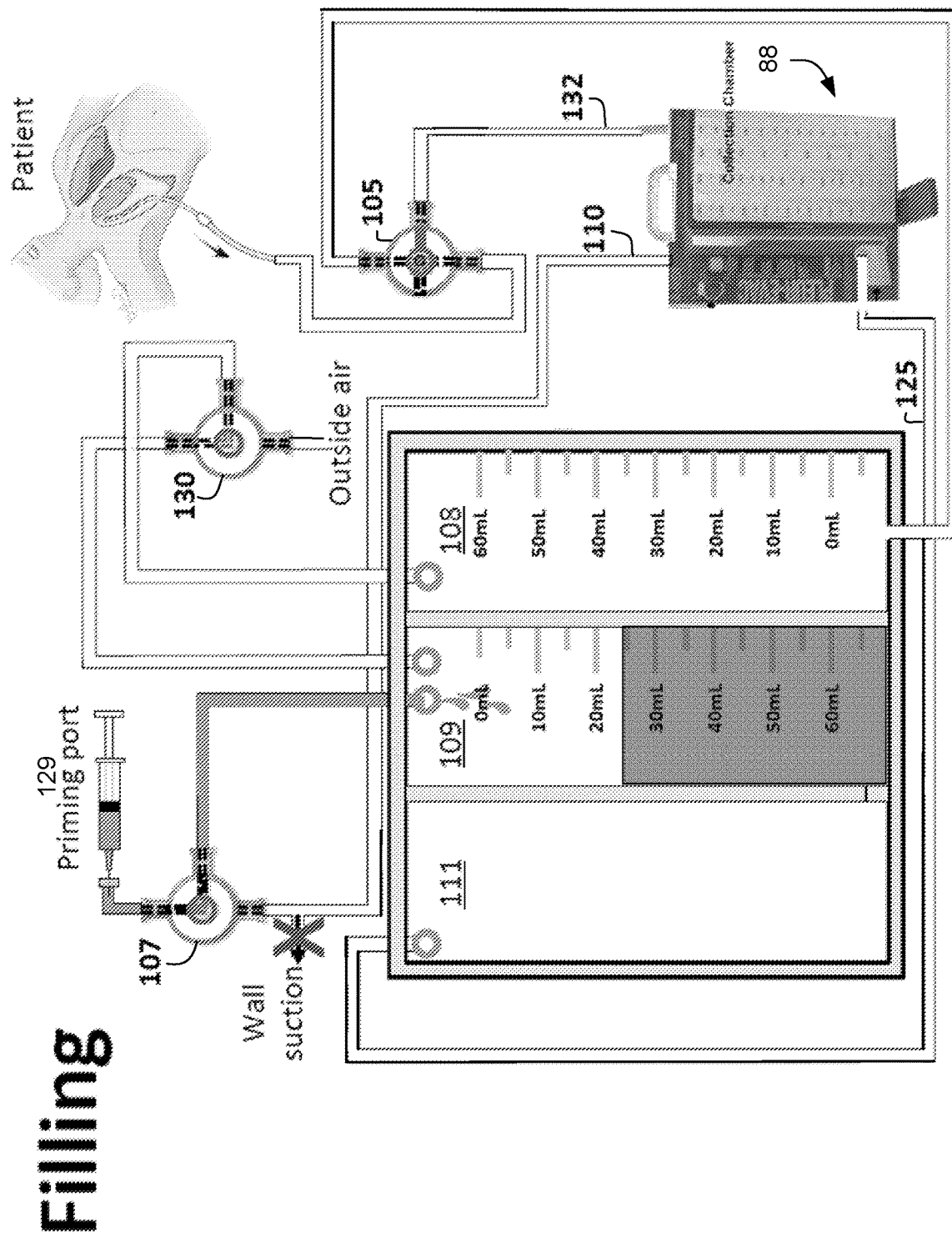
FIG. 14 is an alternate schematic of the gas collection unit of FIG. 5 used in combination with the air evacuation device of FIGS. 2-4 in a filling first mode.

Referring now also to FIGS. 14-17, alternate schematics of system 201 are illustrated. FIG. 14 depicts the filling of chamber 109 with fluid 115, while FIGS. 15-17 correspond with FIGS. 11-13, respectively. In particular, unit 101 is shown in combination with embodiment 88, which is simply a representation of device 99 in production form rather than in schematic form showing collection jars 93, 95, and 97. Valves 105, 130, and 107 are shown with their functional interfaces with chambers 111, 109, and 108 rather than with jars 93, 95, and 97, respectively.

In this form, unit 101 is constructed independently from, but is able to interface with, embodiment 88. As a stand-alone device, unit 101 is specifically configured to be attached to embodiment 88 to allow detection of slow leaks from the patient. The only three interfaces between unit 101 and embodiment 88 are tubings 125, 110, and 132. The ends of these tubings are constructed in such a manner that they may be attached to embodiment 88 in locations where interfaces already exist and connections may be easily effected. Chamber 108 is necessary because there is no ready attachment between chamber 109 and tubing 94; the interface must therefore be with tubes 96 and 132, with chamber 108 as an auxiliary fluid collection chamber.

Figure 15:
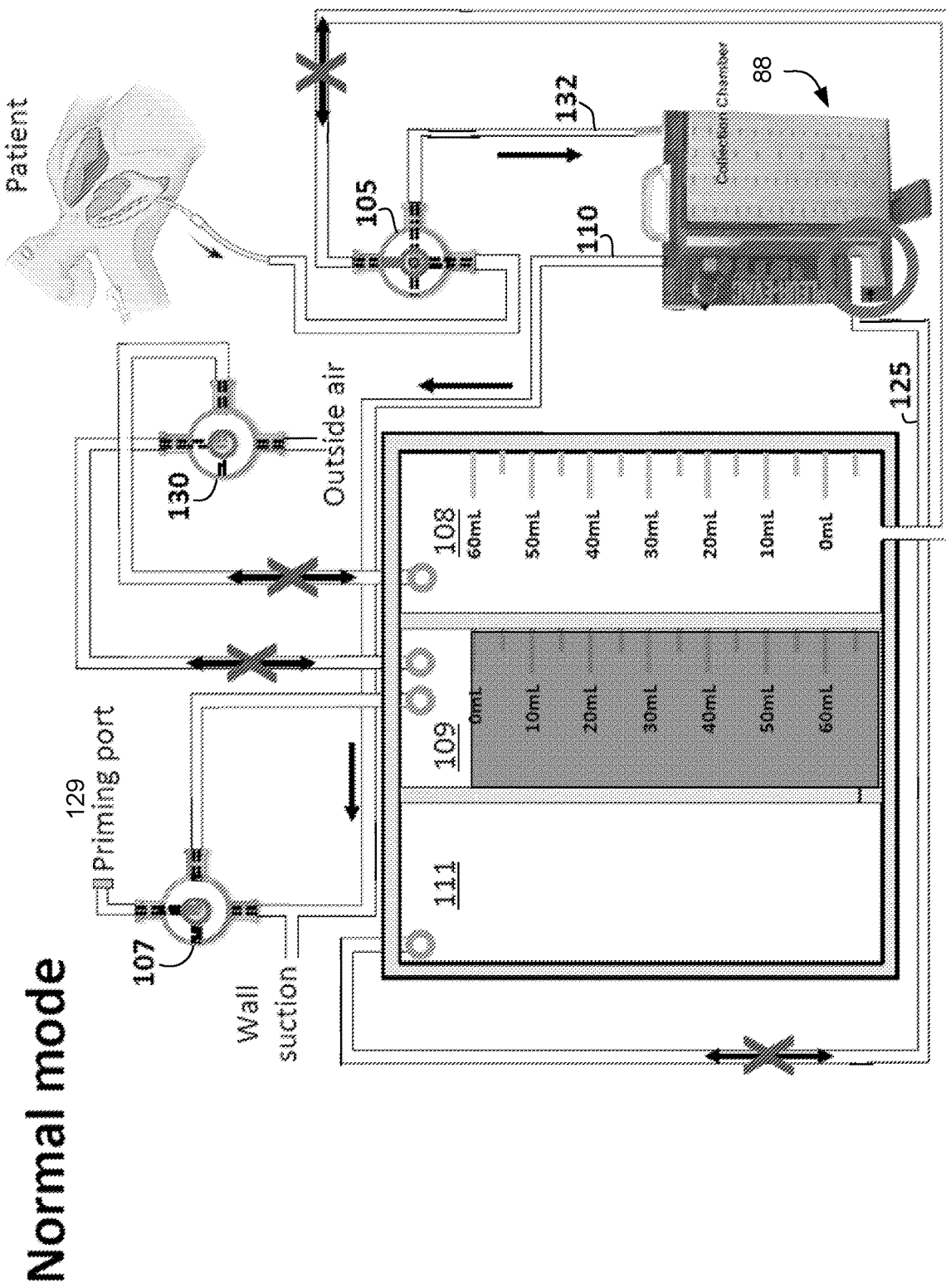
FIG. 15 is an alternate schematic of the gas collection unit of FIG. 5 in combination with the air evacuation device of FIGS. 2-4 in a normal first mode of use.
Figure 16:
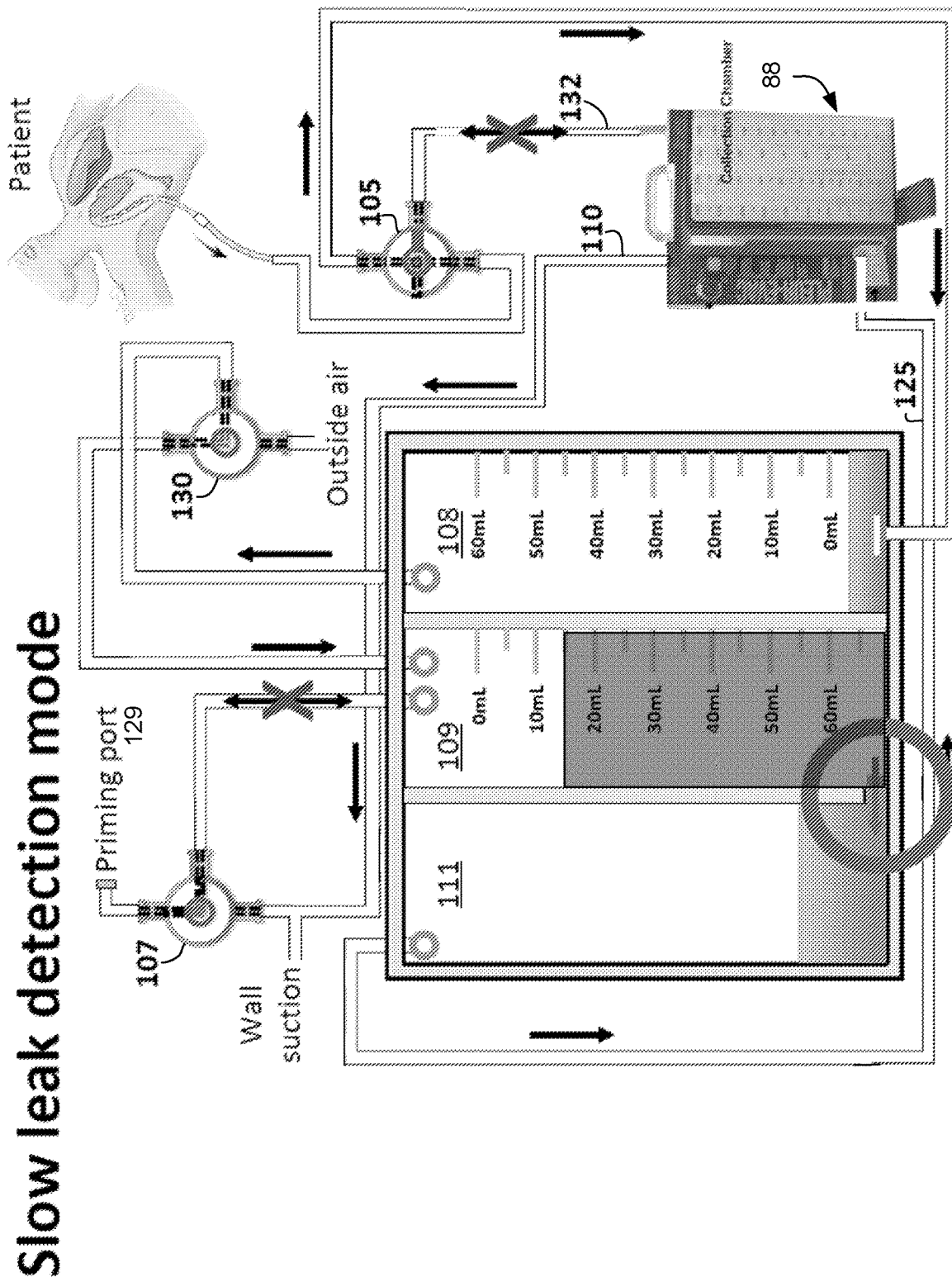
FIG. 16 is an alternate schematic of the gas collection unit of FIG. 5 in combination with the air evacuation device of FIGS. 2-4 in a second mode of use.
Figure 17:
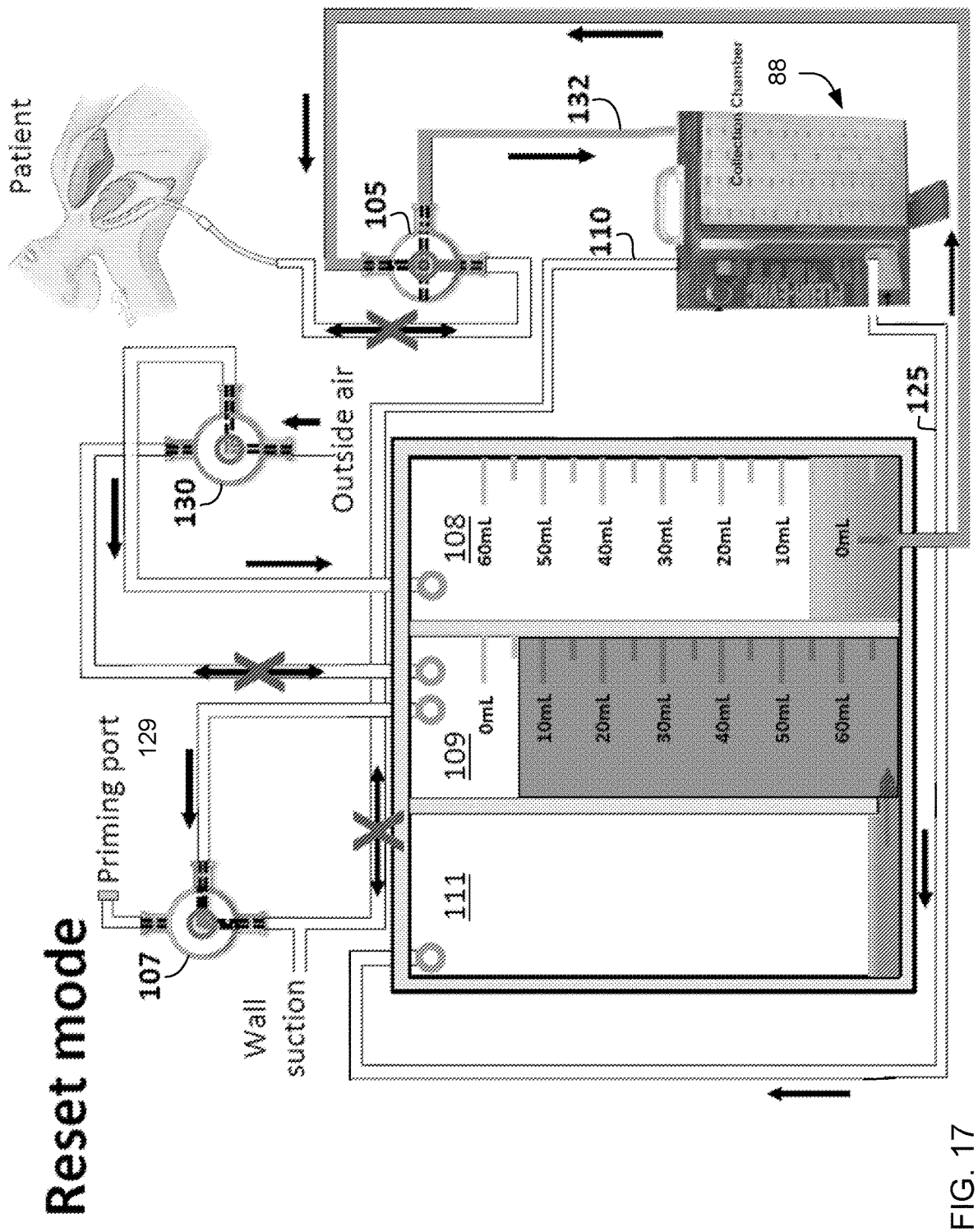
FIG. 17 is an alternate schematic of the gas collection unit of FIG. 5 in combination with the air evacuation device of FIGS. 2-4 in a third mode of use.

When filling, as seen in FIG. 14, with the unit isolated from the patient and non-functional, fluid may be introduced into chamber 109 through priming port 129. In normal mode, as seen in FIG. 15, air is evacuated until bubbling is no longer seen in the water seal chamber of the drainage unit. During the slow leak detection mode, seen in FIG. 16, with the usual regulated suction, any leaked air slowly flows from the patient into chamber 108 thereby displacing fluid into chamber 109. For the reset mode, seen in FIG. 17, following an unsuccessful test, the system is reset by rotating the valve to 'reset' until the fluid has completely returned to chamber 109 and chamber 108 has drained.

Figure 18:
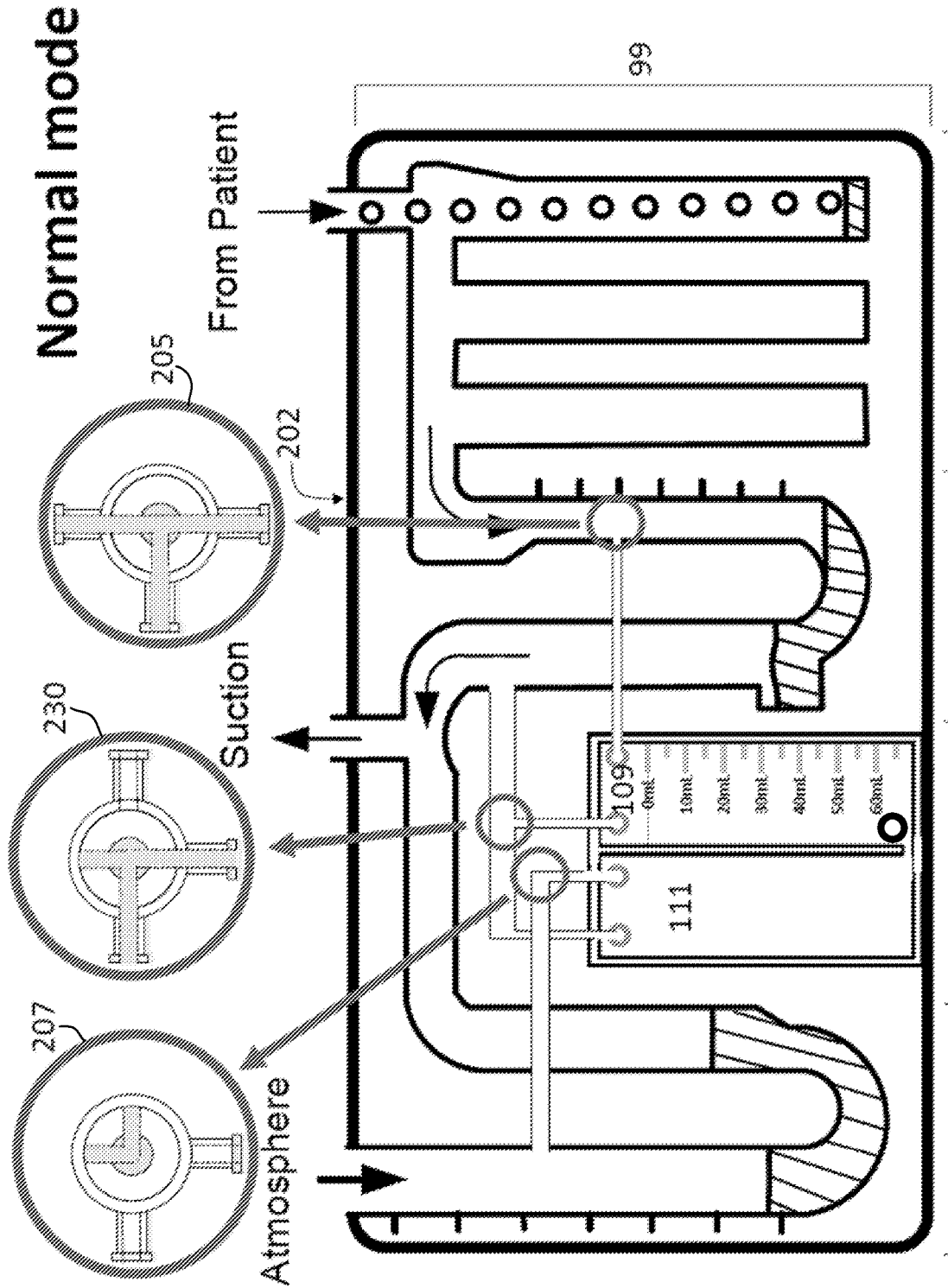
FIG. 18 is an alternate schematic of the gas collection unit of FIG. 5 when integrated with the air evacuation device of FIGS. 2-4 in a first mode of use.
Figure 19:
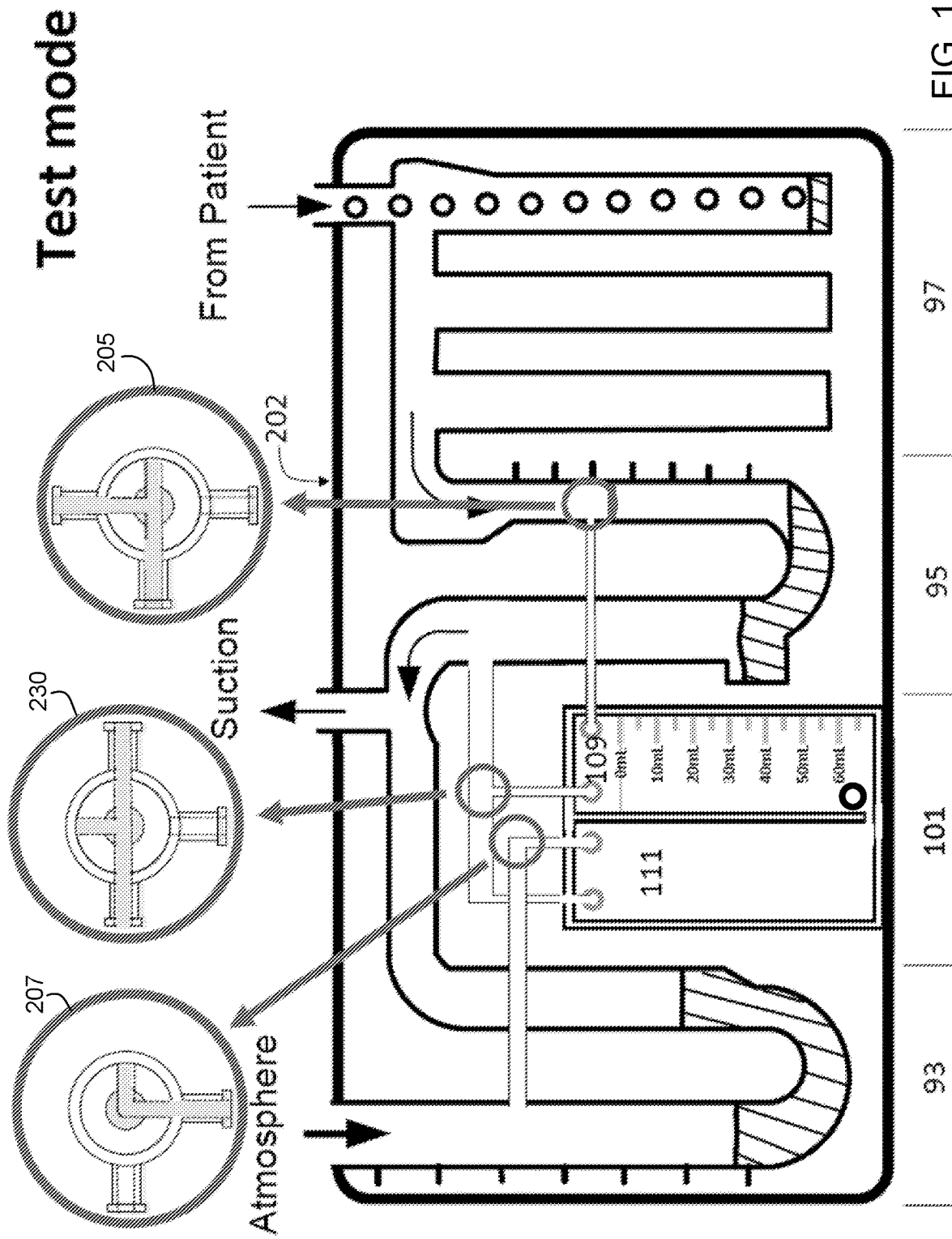
FIG. 19 is an alternate schematic of the gas collection unit of FIG. 5 when integrated with the air evacuation device of FIGS. 2-4 in a second mode of use.
Figure 20:
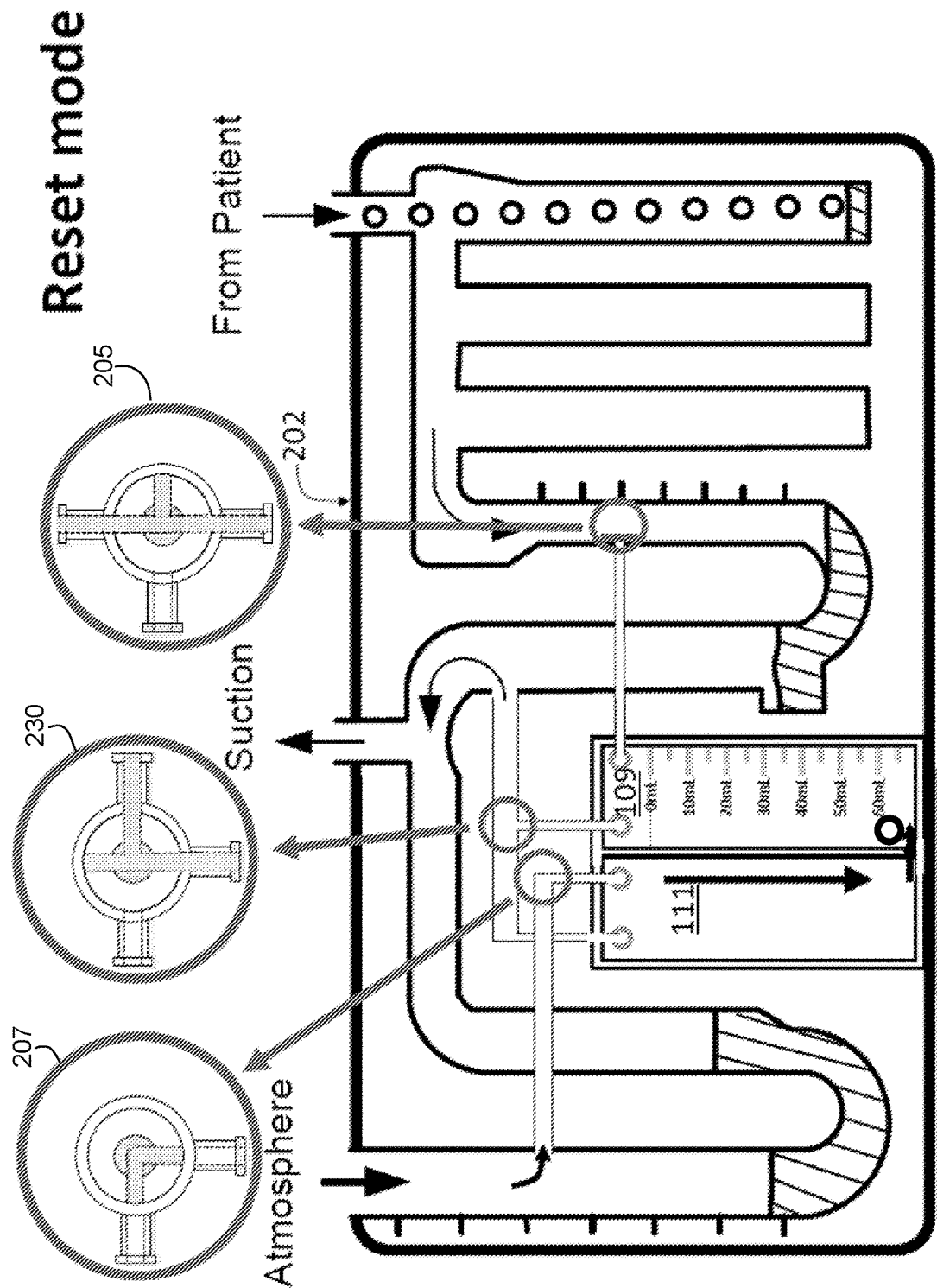
FIG. 20 is an alternate schematic of the gas collection unit of FIG. 5 when integrated with the air evacuation device of FIGS. 2-4 in a third mode of use.

In an alternative embodiment schematically depicted in FIGS. 18-20, unit 101 and device 88 are constructed within a single unit forming an integrated collection and air leak detection system 202. In this construction, and utilizing an alternative system of valves, chamber 108 may be omitted and incorporated into the main collection chamber, which corresponds to bottle 97. By so doing, chamber 108 may be dispensed with by internally integrating it with the collection chamber of embodiment 88, i.e., jar 97. Such simplification is not possible in the case of two stand-alone units as no portal exists in embodiment 88 to which tubing may easily be attached to achieve the desired function. Chambers 109 and 111 continue to operate in parallel with section 95, and testing and resetting functions are both preserved.

Figure 21:
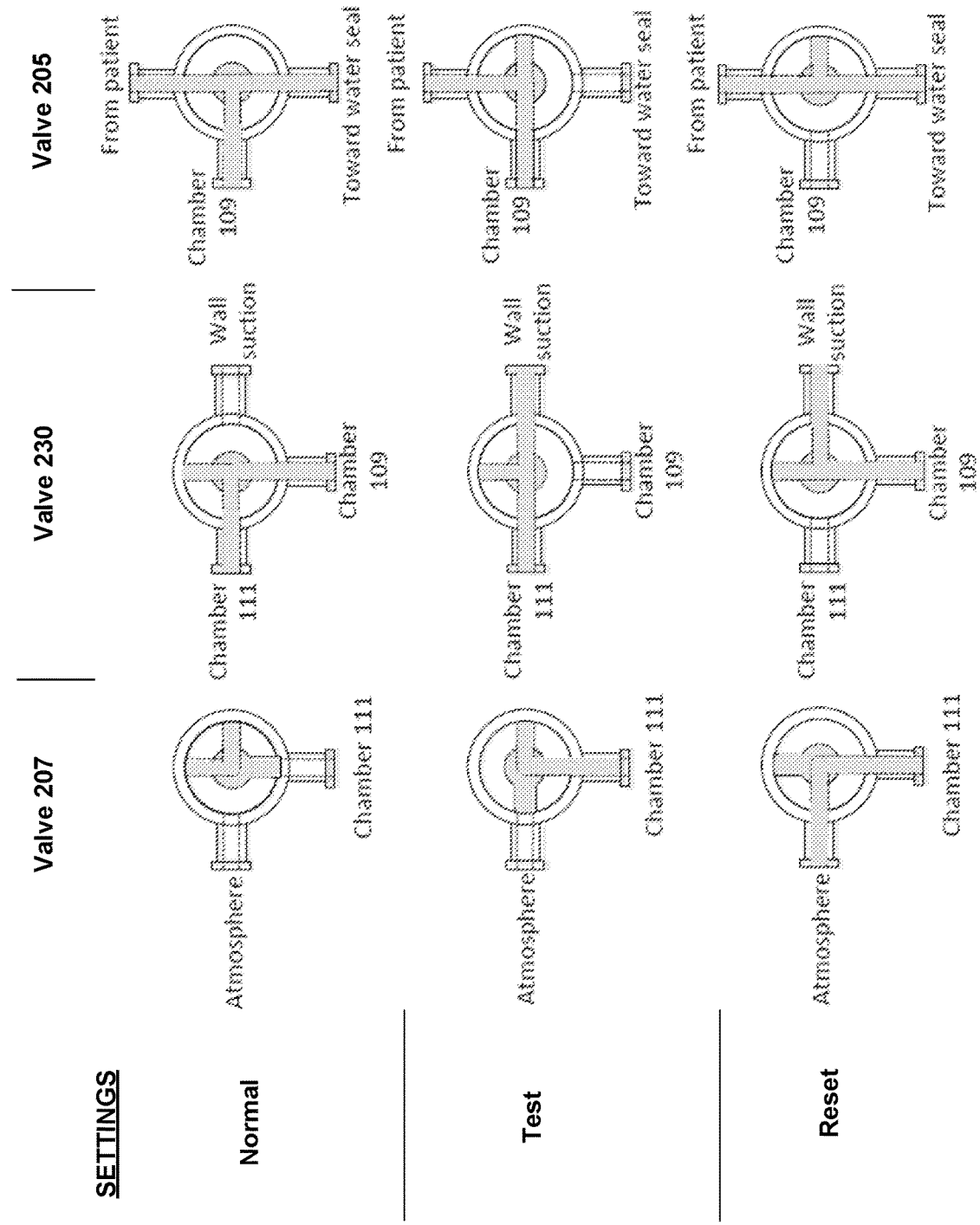
FIG. 21 is a depiction of the settings of the valves shown in FIGS. 18-20.

FIG. 21 summarizes the alternative system of valves 205, 230, and 207 mentioned above. These valves are configured in a manner similar to that depicted in FIGS. 9A-9C and operate in a manner similar to that depicted in FIG. 10. The current application has many advantages over the prior art.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A gas collection unit for use in monitoring and tracking a discharge of air from a patient, comprising:
   a housing containing a first chamber, a second chamber and a third chamber, the chambers being in fluid communication with one another, the housing including a fluid in the second chamber;
   a first valve regulating the passage of air flow from the patient into the first chamber;
   a second valve in communication with the first chamber, the second valve being configured to regulate the passage of air exiting the first chamber for passage into the second chamber; and
   a third valve in communication with the second chamber separate from the second valve, the third valve is subjected to a suction;
   wherein indicia is present on the housing to monitor the movement of fluid into and out of the second chamber; and
   wherein the fluid passes from the second chamber to the first chamber as the first valve is in a closed position and the second valve is in an open position, the fluid passes from the second chamber to the first chamber as air is released from a reset valve.

2. The unit of claim 1, wherein the first valve is a three-way valve.

3. The unit of claim 1, wherein the second and third valves are two-way valves.

4. The unit of claim 1, wherein the first valve is located within a reusable T-connector for communicating with the patient.

5. The unit of claim 1, wherein the first valve is located within a first tube entering the first chamber.

6. The unit of claim 1, wherein actuation of the first valve to an open position directs air flow from the patient into the first chamber.

7. The unit of claim 6, wherein the second valve is closed to prevent air escaping the first chamber, the fluid passes from the first chamber to the second chamber as air is discharged from the patient, the volume of air discharged is collected and measured over a period of time.

8. The unit of claim 1, wherein actuation of the first valve to a closed position prevents air flow from reaching the first chamber.

9. The unit of claim 1, wherein the second valve is located within a second tube exiting the first chamber.

10. The unit of claim 1, wherein the second valve is configured to selectively release pressure within the first chamber.

11. The unit of claim 1, wherein the housing further includes a priming port in the second chamber.

12. The unit of claim 1, wherein the set of valves are coupled together on a similar axis so as to simultaneously rotate between positions.

13. A gas collection system for use in monitoring and tracking a discharge of air from a patient, comprising:
   an air evacuation device including:
      a bottle having a collection tube in communication with the patient;
      a seal chamber in communication with the bottle via a first air tube; and
      a jar in communication with the seal chamber via a second air tube, the jar having a vacuum tube in communication with the interior volume of the jar, the jar being under vacuum pressure; and
   a gas collection unit including:
      a housing containing a first chamber, a second chamber and a third chamber, the chambers being in fluid communication with one another, the housing including a fluid in the second chamber,
      a first valve regulating the passage of air flow from the patient into the first chamber;
      a second valve in communication with the first chamber, the second valve being configured to regulate the passage of air exiting the first chamber for passage into the second chamber; and
      a third valve in communication with the second chamber separate from the second valve, the third valve is subjected to a suction;
      wherein indicia is present on the housing to monitor the movement of fluid into and out of the second chamber;
   wherein operation of the set of valves changes modes of use.

14. The system of claim 13, wherein the first valve is a three-way valve permitting air and fluid to pass into either of the first chamber and the bottle.

15. The system of claim 13, wherein the second valve is a two-way valve selectively permitting the release of air to the vacuum tube.

16. The system of claim 13, wherein the amount of air discharged by the patient is measured over time through the gas collection unit, the first valve being in an open position and the second valve being in a closed position.

17. The system of claim 16, wherein the second valve is selectively opened to reset the fluid level within the housing.

18. The system of claim 13, wherein the first valve is in a closed position to pass the air and fluid into the bottle, the air being visibly passed through the seal chamber, the seal chamber showing the instantaneous discharge of air.

19. The system of claim 13, wherein the set of valves are coupled together on a similar axis so as to simultaneously rotate between positions.

* * * * *